(12) United States Patent
Posner et al.

(10) Patent No.: US 11,337,547 B1
(45) Date of Patent: May 24, 2022

(54) INGREDIENT LEVEL CONSUMPTION GUIDANCE IN A BEVERAGE DISPENSING SYSTEM

(71) Applicant: Cana Technology, Inc., Redwood City, CA (US)

(72) Inventors: Nicholas D. Posner, Redwood City, CA (US); Anthony Prats, San Francisco, CA (US); Shaun Lind, Sausalito, CA (US)

(73) Assignee: Cana Technology, Inc., Redwood City, CA (US)

( * ) Notice: Subject to any disclaimer, the term of this patent is extended or adjusted under 35 U.S.C. 154(b) by 0 days.

(21) Appl. No.: 17/550,233

(22) Filed: Dec. 14, 2021

(51) Int. Cl.
| | |
|---|---|
| *A47J 31/52* | (2006.01) |
| *G06K 7/10* | (2006.01) |
| *G06Q 30/06* | (2012.01) |
| *G05B 19/042* | (2006.01) |
| *A47J 31/40* | (2006.01) |
| *A47J 31/41* | (2006.01) |
| *G16H 50/70* | (2018.01) |
| *G16H 20/60* | (2018.01) |
| *G16H 40/67* | (2018.01) |
| *G16H 15/00* | (2018.01) |
| *G06Q 30/02* | (2012.01) |

(52) U.S. Cl.
CPC .......... *A47J 31/525* (2018.08); *A47J 31/402* (2013.01); *A47J 31/41* (2013.01); *A47J 31/521* (2018.08); *G05B 19/042* (2013.01); *G06K 7/10297* (2013.01); *G06Q 30/0631* (2013.01); *G05B 2219/2645* (2013.01); *G06Q 30/0206* (2013.01); *G16H 15/00* (2018.01); *G16H 20/60* (2018.01); *G16H 40/67* (2018.01); *G16H 50/70* (2018.01)

(58) Field of Classification Search
CPC ...... A47J 31/525; A47J 31/521; A47J 31/402; A47J 31/41; G06K 7/10297; G06Q 30/0631; G06Q 30/0206; G05B 19/042; G05B 2219/2645; G16H 50/70; G16H 20/60; G16H 40/67; G16H 15/00
See application file for complete search history.

(56) References Cited

U.S. PATENT DOCUMENTS

| | | | | |
|---|---|---|---|---|
| 7,295,889 | B2* | 11/2007 | Lahteenmaki | G16H 20/60 700/239 |
| 7,762,181 | B2* | 7/2010 | Boland | A47J 31/525 99/321 |
| 10,464,800 | B2* | 11/2019 | Hevia | G07F 9/026 |
| 10,611,622 | B2* | 4/2020 | Kline | G07F 9/009 |
| 10,674,857 | B2* | 6/2020 | Lyons | A47J 31/005 |
| 10,913,647 | B2* | 2/2021 | Lyons | B67D 1/0079 |

(Continued)

*Primary Examiner* — Michael Collins
(74) *Attorney, Agent, or Firm* — Daylight Law, P.C.

(57) ABSTRACT

Ingredient level consumption guidance methods and control systems in beverage mixture dispensing systems are disclosed. A disclosed method for operating a beverage mixture dispensing system includes setting an ingredient consumption threshold for an ingredient. The ingredient consumption threshold is associated with an account. The method also includes mixing a beverage using an amount of the ingredient, dispensing the beverage, updating an ingredient consumption level associated with the account, by adding the amount to the ingredient consumption level, and displaying, on a display, the ingredient consumption level and the ingredient consumption threshold.

30 Claims, 5 Drawing Sheets

(56) References Cited

U.S. PATENT DOCUMENTS

| | | | |
|---|---|---|---|
| 11,091,361 B2* | 8/2021 | Joshi | B67D 1/0871 |
| 2013/0218602 A1* | 8/2013 | Lahteenmaki | G06Q 10/10 |
| | | | 705/3 |
| 2015/0144653 A1* | 5/2015 | Kline | G07F 9/001 |
| | | | 222/23 |
| 2016/0306931 A1* | 10/2016 | Lahteenmaki | G16H 40/67 |
| 2018/0168385 A1* | 6/2018 | Boone | G06Q 30/0621 |
| 2018/0240359 A1* | 8/2018 | Hujsak | G06N 20/00 |
| 2018/0328775 A1* | 11/2018 | Gurumohan | B67D 3/0093 |

* cited by examiner

INGREDIENT LEVEL CONSUMPTION GUIDANCE IN A BEVERAGE DISPENSING SYSTEM

BACKGROUND

Beverage mixture dispensing systems mix various components, such as carbonated water and flavored syrups, to create and dispense beverages. Certain beverage mixture dispensing systems are configured to make a variety of beverages using different flavors components. For example, a traditional soda fountain is designed to dispense different flavored sodas by mixing different syrups with carbonated water. In keeping with this traditional example, beverage mixture dispensing systems in general are designed to dispense one type of drink such as soft drinks, coffee, beer, etc. It is uncommon for a single beverage mixture dispensing system to be capable of producing all the many different beverages that a user may wish to consume throughout the course of the day and night—from coffee to cocktails.

SUMMARY

Ingredient level consumption monitoring and control systems for beverage mixture dispensing systems are disclosed. In specific embodiments of the invention disclosed herein the disclosed beverage mixture dispensing systems are designed to create a broad array of beverages using base ingredients as opposed to premixed syrups for specific flavors or packaged flavor pods. Such beverage mixture dispensing systems can create all, or substantially all, of the drinks that a given user may require throughout the day. In specific embodiments of the invention disclosed herein, the disclosed beverage mixture dispensing systems are designed to monitor and control, at the ingredient level, an amount of the various ingredients that a user ingests via the beverages it dispenses.

In specific embodiments of the invention, the ingredient consumption monitoring and control systems disclosed herein could set an ingredient consumption threshold for an ingredient. The thresholds could be set by a user or automatically by the system. The ingredient consumption threshold could be a maximum ingredient consumption threshold. For example, a user could determine that they would like to keep their sugar intake below 50 grams per day and set an ingredient consumption threshold for sugar on the system to that amount. The systems disclosed herein could then track this information for the user, display the ingredient consumption level for sugar throughout the day, and assist the user in selecting beverages that would prevent them from exceeding the specified ingredient consumption threshold. In specific embodiments, the systems could prevent the device from dispensing beverages that exceeded the specified ingredient consumption threshold.

Alternatively, or in combination, in specific embodiments of the invention, the ingredient consumption monitoring and control systems disclosed herein could set an ingredient minimum consumption threshold which would specify the amount of an ingredient that they did want to consume. The thresholds could be set by a user or automatically by the system. For example, a user could determine that they wanted to consume 20 mg per day of vitamin C and set an ingredient minimum consumption threshold for vitamin C to that amount. The systems disclosed herein could then track this information for the user, present the ingredient consumption level consumed so far throughout the day, and assist the user in selecting beverages that would lead them to exceed the specified ingredient minimum consumption threshold.

In specific embodiments of the invention, a method for operating a beverage mixture dispensing system is provided. The method comprises setting an ingredient consumption threshold for an ingredient. The ingredient consumption threshold is associated with an account (e.g., including a user profile of an account holder) or a subaccount (e.g., including a user profile managed under the account). The method also comprises mixing a beverage using an amount of the ingredient, dispensing the beverage, updating an ingredient consumption level associated with the account, by adding the amount to the ingredient consumption level, and displaying, on a display, the ingredient consumption level and the ingredient consumption threshold.

In specific embodiments of the invention, a beverage mixture dispensing system is provided. The beverage mixture dispensing system comprises a dispenser, a display, a set of ingredient reservoirs storing a respective set of ingredients, and one or more computer readable media storing instructions which, when executed by one or more processors, cause the beverage mixture dispensing system to: set an ingredient consumption threshold for an ingredient, wherein the ingredient consumption threshold is associated with an account, and wherein the ingredient is in the respective set of ingredients; mix a beverage using an amount of the ingredient from the set of ingredient reservoirs; dispense the beverage using the dispenser; update an ingredient consumption level associated with the account by adding the amount to the ingredient consumption level; display, on the display, the ingredient consumption level and the ingredient consumption threshold; and store this information in a database or other information storage system.

In specific embodiments of the invention, one or more computer-readable media storing instructions are provided. The instructions, when executed by one or more processors in a beverage mixture dispensing system, cause the beverage mixture dispensing system to execute a method comprising: setting an ingredient consumption threshold for an ingredient, wherein the ingredient consumption threshold is associated with an account; mixing a beverage using an amount of the ingredient; dispensing the beverage; updating an ingredient consumption level associated with the account, by adding the amount to the ingredient consumption level; and displaying, on a display, the ingredient consumption level and the ingredient consumption threshold.

BRIEF DESCRIPTION OF THE DRAWINGS

In the figures, like reference numbers correspond to like components unless otherwise stated.

DETAILED DESCRIPTION

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Ingredient level consumption monitoring and control systems for beverage mixture dispensing systems are disclosed in detail in this disclosure. The methods and systems disclosed in this section are nonlimiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

Beverage mixture dispensing systems in accordance with specific embodiments disclosed herein can include one or more ingredient reservoirs such as one or more solvent reservoirs and one or more concentrated ingredient reservoirs. The beverage mixture dispensing systems can be designed to mix various beverages using various sets of ingredients selected from those available to the device. The solvent reservoirs can contain solvents such as water, alcohol (e.g., ethanol or isopropanol), and other solvents. The concentrated ingredient reservoirs can also include high-volume concentrated ingredient components such as a sweetening liquid. The sweetening liquid can be an artificial sweetener (aspartame, saccharin, sucralose, acesulfame K, etc.) or natural sweetener (e.g., glucose, fructose, sucrose, etc.) dissolved in a solvent such as liquid water. The reservoirs can be standalone cartridges filed with the ingredients and attached to the beverage mixture dispensing system or an external source of the ingredients which is connected to a socket on the device (e.g., a faucet or other external solvent supply source). The concentrated ingredient reservoirs can contain concentrated ingredients that are meant to be combined with the solvents from the solvent reservoirs to make a beverage. The systems can include mixing areas in which solvents from the solvent reservoirs are combined with concentrated ingredients from the concentrated ingredient reservoirs.

Figure 1A:
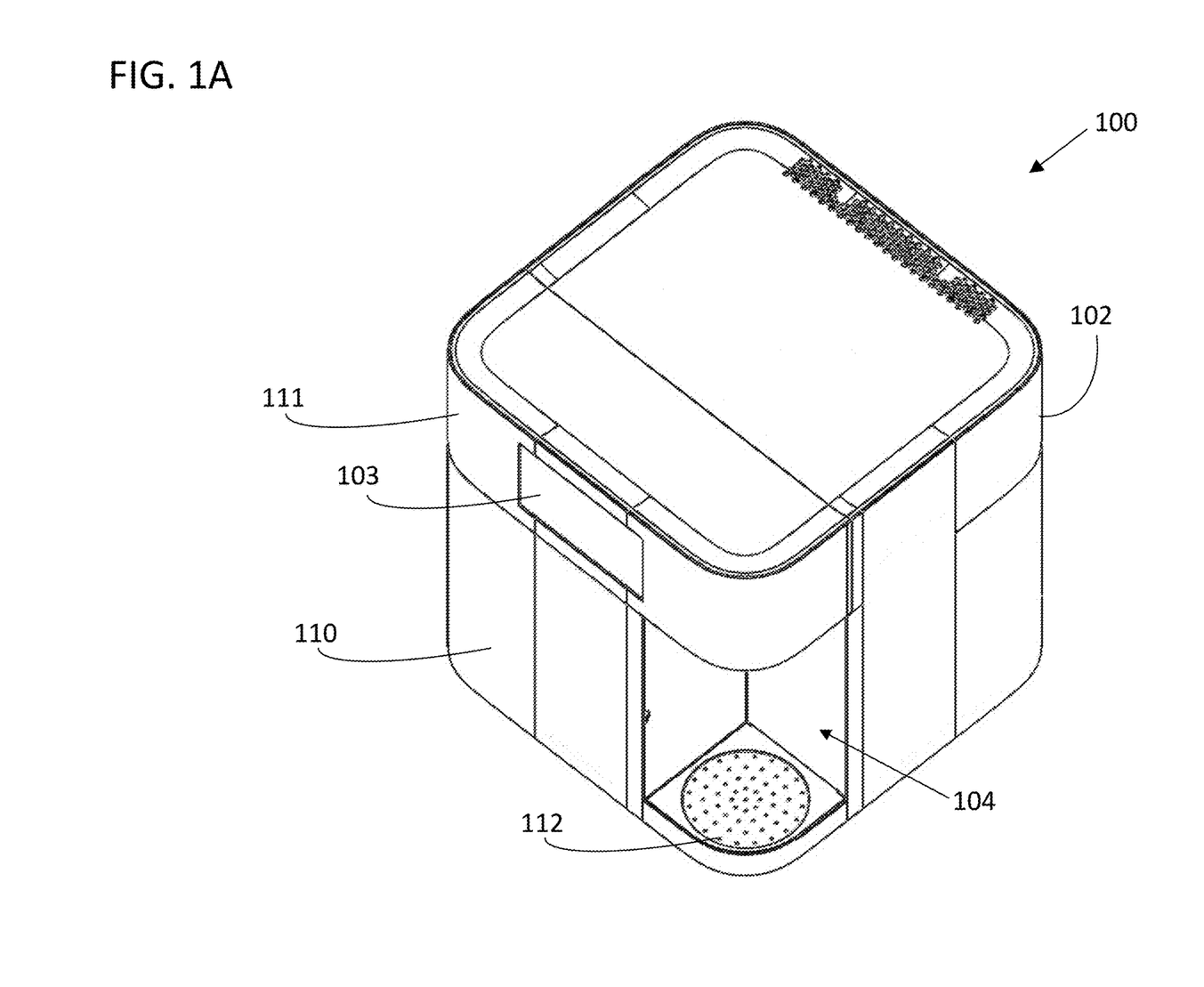
FIG. 1A illustrates a beverage mixture dispensing device that can be utilized in accordance with specific embodiments of the invention disclosed herein.

FIG. 1A illustrates an example of a beverage mixture dispensing device 100, in accordance with specific embodiments disclosed herein. The beverage mixture dispensing device 100 can be a beverage mixture dispensing system on its own or it can be combined with one or more servers, alternative peer devices of the same type, and/or one or more separate devices such as one or more smartphones to form a beverage mixture dispensing system. The beverage mixture dispensing device 100 can be any of the fluid mixture dispensing devices described in U.S. Provisional Patent Application No. 63/146,461 filed Feb. 5, 2021, which is incorporated by reference herein in its entirety for all purposes.

The beverage dispensing device 100 can include a casing, such as casing 102, that can house various internal components of the device. The casing 102 can include various accesses to the interior of the device. The accesses can be in the form of doors, such as upper access door 111 and lower access door 110. The accesses can also be removable portions, such as lids or walls of the casing. The accesses can be configured so that a user of the device can access at least part of the interior of the device, for example to replace a component, to clean the device, etc.

The beverage dispensing devices disclosed herein can also include a user interface, such as display 103. The user interfaces can include any means for outputting information from the device to a user of the device, and for inputting information from the user of the device to the device. In this way, the user interface can include any means that facilitate the interaction of a user of the device with the device, including but not limited to a display, a speaker, a microphone, a camera, various sensors such as light and presence sensors, etc. For example, the user interface can include a touch screen display, so that the device can display information for the user via the display, and the user can provide inputs to the device via the touch screen display. As another example, the interaction between the user and the device can be via auditory cues provided by the device via a speaker and voice commands from the user received via a microphone. As another example, the device can recognize user facial expressions and gestures via cameras and sensors. The user interface components can be associated to a controller of the device so that the controller can administrate the information to be outputted and process the information being received.

The user interface can be integrated with the device itself or provided on a separate device (e.g., a personal computer or smartphone). The separate device can be in communication with the device through a network (e.g., via a web portal or a dedicated application). In these embodiments, control signals can be sent to the device from the separate device remotely through the network.

As used in this disclosure the noun "display" refers to a physical display such as a touch display or computer screen while the verb "display" refers to presenting something on such displays. Furthermore, as used in this disclosure, the verb "display," when used with reference to two items (e.g., "A and B are displayed") does not require that the two items are displayed at the same time on such displays and should be interpreted to include the concept of the two items being separately presented on the display at two different times.

The beverage dispensing device 100 can also include a dispense area, such as dispense area 104. Dispense area 104 can be the area where a beverage is dispensed out of the device 100. Dispense area 104 can be an area configured to receive a vessel or other containers to dispense a beverage out of device 100. The dispense area 104 can be sized so that different containers (for example a wine glass) can be placed therein. In specific embodiments of the invention, the dispense area 104 can be adjusted, for example by using a height adjustable tray. The dispense area 104 can include a waste outlet, such as waste outlet 112. The waste outlet can be a removable waste outlet, such as a removable drip tray. The dispense area can also include one or more sensors such as a radio frequency reader to interrogate vessels placed in the dispense area 104. The reader could be located within casing 102 directly behind either of the two vertical surfaces of dispense area 104. The radio frequency reader could be an RFID or NFC reader and could be designed to identify a specific vessel being placed in or near dispense area 104. Alternative sensors such as an electromagnetic, visible light, or other sensor can be used to identify one or more features of a vessel placed in or near dispense area 104.

Figure 1B:
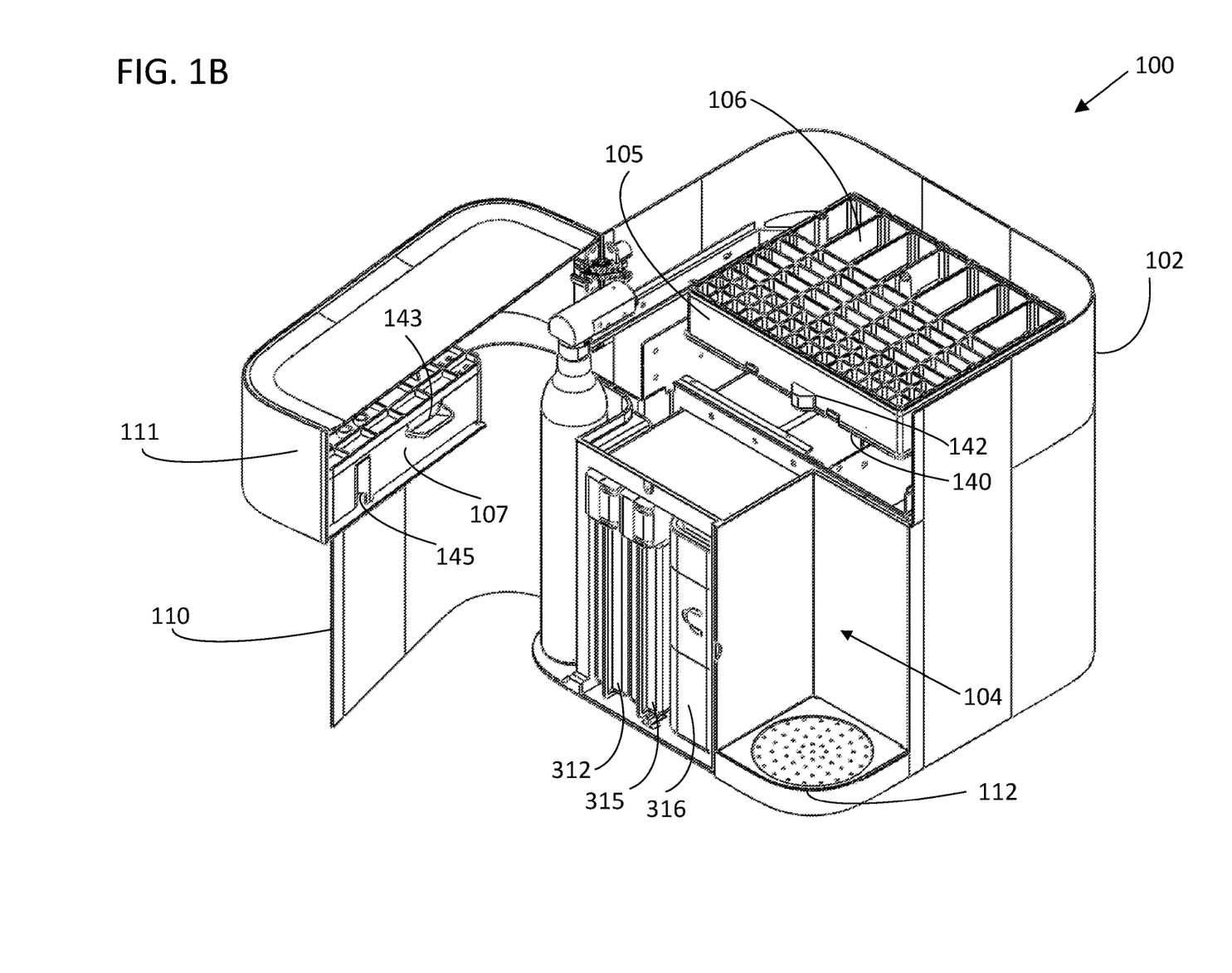
FIG. 1B illustrates the interior of the beverage mixture dispensing device from FIG. 1A that can be utilized in accordance with specific embodiments of the invention disclosed herein.

FIG. 1B illustrates the beverage dispensing device 100 of FIG. 1A in an open configuration to illustrate exemplary internal components that can be housed by the casing 102 of the beverage dispensing device 100, in accordance with specific embodiments disclosed herein. The accesses, such as upper access door 111 and the lower access door 110, are open in this figure. The doors can be attached to the remaining of the casing via hinges or other structure. The doors can alternatively be removable doors so that they are completely removed when open. The doors can be any kind of doors such as sliding doors, and open in any direction, for example to the top or to the right of the device. Doors 111 and 110 can be separate doors or a unitary door of the device. In this example, the access doors have been represented in the front wall of the device. However, this is not a limitation of the invention. Different doors and/or any access to the interior of the device can be located anywhere on the device, and do not need to be located on the front wall. In the example of FIG. 1B, a portion of the top wall of the device 100 has been removed to expose some additional exemplary components of the device.

The beverage dispensing device 100 can include one or more ingredient reservoirs, such as ingredient reservoir 106. The ingredient reservoirs can store ingredients to be used by the beverage dispensing device 100 to create a beverage, such as concentrated liquids (e.g., flavor syrups, salts, acids, etc.) The ingredient reservoirs can be any of the ingredient reservoirs described in U.S. patent application Ser. No. 17/545,699 filed Dec. 8, 2021, which is incorporated by reference herein in its entirety for all purposes. The ingredients can be stored in the ingredient reservoirs as molecular entities independently suspended in a solvent, such as liquid water. In specific embodiments of the invention, the ingredients are stored in the ingredient reservoirs as molecular entities in liquid form. As used herein the term "molecular entity" refers to any constitutionally or isotopically distinct atom, molecule, ion, ion pair, radical, radical ion, complex, conformer, etc. which is identifiable as a separately distinguishable entity and that can be used to concisely identify a chemical in a chemical process or reaction.

The ingredient reservoirs, such as ingredient reservoir 106, can be located in a cartridge, such as cartridge 105. The cartridge can be accessed via one of the accesses of the device. For example, the cartridge can be accessed through upper access door 111. In this way, a user of the device can replace the cartridge as needed. In the example of FIG. 1B, the top surface of cartridge 105 has been removed to expose the ingredient reservoirs 106. However, the cartridge can be completely encased. In specific embodiments of the invention, the cartridge includes a removable lid so that the various ingredient reservoirs can be accessed, for example to be refilled. The cartridge can be any of the cartridges described in U.S. Provisional Patent Application No. 63/146,461 filed Feb. 5, 2021, U.S. patent application Ser. No. 17/547,081 filed Dec. 9, 2021, U.S. patent application Ser. No. 17/547,612 filed Dec. 10, 2021, and U.S. patent application Ser. No. 17/545,699 filed Dec. 8, 2021, all of which are incorporated by reference herein in their entirety for all purposes.

The beverage dispensing device 100 can also include one or more high volume reservoirs, such as first reservoir 316, second reservoir 312, and third reservoir 315. The solvent reservoirs can store solvents to be used by the beverage dispensing device 100 to create a beverage, such as water, alcohol, etc. The solvent reservoirs can be any of the solvent reservoirs described in U.S. Provisional Patent Application No. 63/146,461 filed Feb. 5, 2021 and U.S. patent application Ser. No. 17/547,081 filed Dec. 9, 2021, all of which are incorporated by reference herein in their entirety for all purposes. The solvent reservoirs can be accessed via one of the accesses of the device. For example, the solvent reservoirs can be accessed through lower access door 110. In this way, a user of the device can remove the solvent reservoirs as needed, for example to refill a water tank.

The beverage dispensing device 100 can be configured to create a beverage by mixing one or more ingredients from one or more concentrated ingredient reservoirs 106 and/or one or more high volume reservoirs 316, 312, 315. A controller of the system can have knowledge of the amount of each compound needed for a given recipe and cause the device to dispense the required amount of concentrated ingredients and/or solvent to a mixing area of the device. As such, the controller can have direct knowledge of how much of each ingredient in the system is added to a dispensed beverage. The mixing area can be formed on a bottom plate, such as plate 140, of the ingredient cartridge. Ingredients from the ingredient reservoirs 106 and solvent from the solvent reservoirs 316, 312, 315 can flow from the respective reservoirs to the mixing area of the device 100. In specific embodiments of the invention, the ingredients from the ingredient reservoirs 106 flow to the mixing area and solvent from the reservoirs flow though the mixing area to "collect" the ingredients dispensed therein. In specific embodiments of the invention, solvent from the reservoirs is allowed to enter the mixing area, and the concentrated ingredients from the concentrated ingredient reservoirs are dispensed from the reservoirs directly into the solvent already in the mixing area. In any case, an intermediate mixture of one or more concentrated ingredients and/or one or more solvents can be formed in the mixing area of the device.

The term "intermediate mixture" is used herein to refer to a mixture being created in the mixing area of the device (for example in one or more mixing channels formed on plate 140). FIG. 1B illustrates a fluid outlet 142 of the cartridge. Fluid outlet 142 can be connected to the mixing area and allow the intermediate mixture formed therein to flow out to a final dispense chamber 107. The final dispense chamber can be any of the final dispense chambers described in U.S. Provisional Patent Application No. 63/146,461 filed Feb. 5, 2021, and U.S. patent application Ser. No. 17/548,318 filed Dec. 10, 2021, all of which are incorporated by reference herein in their entirety for all purposes.

When the access door 111 is closed, the final dispense chamber 107 can be connected to the fluid outlet 142 of the cartridge via the fluid inlet 143. Once in the final dispense chamber 107, the intermediate mixture can be turned into the final beverage to be dispensed by the device 100. In specific embodiments of the invention, the final beverage is the intermediate mixture itself, as received from the mixing area. Alternatively, or in combination, the intermediate mixture can be further mixed with other ingredients (for example sugar water, carbonated water, etc.) in the final dispense chamber to create the final beverage. Alternatively, or in combination, the intermediate mixture can be submitted to other processes such as further mixing, temperature adjustments, carbonation, etc. in the final dispense chamber 107 to create the final beverage. The final beverage can then be dispensed out the final dispense chamber 107 and to the dispense area 104 via a dispenser, such as dispenser 145.

Ingredient level consumption and guidance methods for systems such as the ones described above with reference to FIGS. 1A and 1B are described below with reference to FIGS. 2-4. However, while the methods can be used with such devices, they are more broadly applicable to any beverage mixture dispensing system. The beverage mixture dispensing systems disclosed herein can include controllers, such as a local controller 211 located inside a beverage mixture dispensing system 210, or remote controllers in separate devices such as smartphone 212 or cloud architecture 213, which are configured to execute the steps of the methods described herein by sending control signals to and receiving information signals from various user interfaces, pumps, valves, pneumatic systems, sensors, actuators, and other devices that can be utilized to mix a beverage, collect information, provide information to a user, and monitor the mixing process. The controller can include one or more processors and can have access to one or more computer-readable media storing instructions which, when executed by the one or more processors, cause the beverage mixture dispensing system to operate in accordance with the methods disclosed herein.

Figure 2:
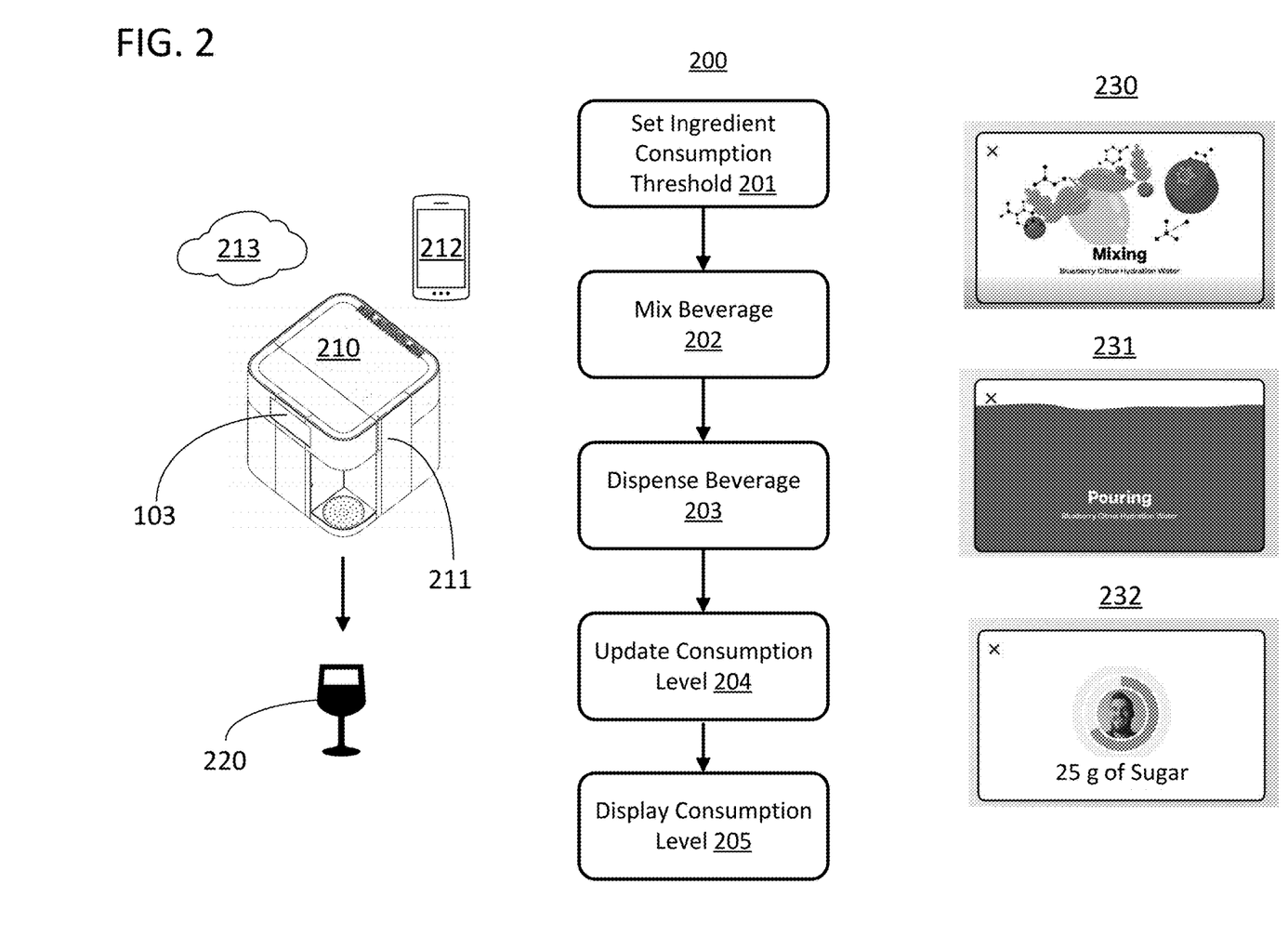
FIG. 2 illustrates a flow chart for a set of methods in accordance with specific embodiments of the invention disclosed herein.

FIG. 2 illustrates a flow chart 200 for a set of methods for operating a beverage mixture dispensing system. The beverage mixture dispensing systems disclosed herein can be operated in accordance with the methods represented by flow chart 200. The methods for operating a beverage mixture dispensing system represented by flow chart 200 include methods for monitoring an ingredient consumption level for an ingredient using a device and displaying an ingredient consumption level to a user. Specific embodiments of the methods represented by flow chart 200 include additional steps to assist in the monitoring and control of the consumption level of the ingredient.

In specific embodiments of the invention, an ingredient consumption threshold for an ingredient can be set. As such, flow chart 200 includes a step 201 of setting an ingredient consumption threshold for an ingredient. The ingredient consumption threshold can be set in response to a receipt of instructions from a user, by an algorithmic calculation or predictive model based on the user's actions, or by default. For example, a user can use the user interface of a beverage mixture dispensing system to select the ingredient consumption threshold using a threshold selector widget presented on a touch screen display of a beverage mixture dispensing system or on a separate device such as a smartphone. An ingredient consumption threshold is an amount of a specific ingredient that a user would like to consume less of or more than. For example, the ingredient consumption threshold could be an ingredient consumption maximum threshold specifying a limit on the amount of a given ingredient that a user would like to consume. As another example, the ingredient consumption threshold could be an ingredient consumption minimum threshold specifying a minimum amount of a given ingredient that a user would like to consume. The ingredient consumption threshold can be set with respect to an ingredient in the form of an independent molecular entity (e.g., $H_2O$, ethanol, or caffeine) or with respect to an ingredient in the form of a family of compounds (e.g., alcohol, salt, food grade acids, food grade bases, artificial sweeteners, sweeteners, sugar, etc.).

While the ingredient consumption threshold are amounts of specific ingredients, they can be set indirectly by a user without reference to specific amounts. In the example provided above, a user specified a numeric value, in milligrams, of an ingredient to set the threshold. However, a user could also specify the threshold in terms of a percentage of a recommend daily value, or a percentage of historical consumption by the user (e.g., set the threshold to 75% of a current ingredient intake). The historical consumption could be tracked by the device and the device could present this option to the user without the user needing to know what their exact historical consumption level was. A user could also choose to have the threshold changed continually to assist in altering their consumption gradually. For example, a user could select a gradual tapering option to change the threshold overtime to decreasing or increasing percentages of a baseline value. A user could also specify an ingredient threshold indirectly by selecting from various programs such as a "hydration," "low sugar," "healthy," "low acid," or "immunity boost" programs where the selection of such programs automatically set one or more ingredient consumption thresholds without the user having to specify numerical thresholds with respect to one or more ingredients.

In specific embodiments of the invention, the beverage mixture dispensing system could recommend or set a threshold for a user. For example, the beverage mixture dispensing device could identify an unhealthy trend in the user's consumption pattern, such as an increasing intake of an unhealthy ingredient, and suggest setting a threshold for one or more ingredients or for adopting one of the programs mentioned in the prior paragraph. The beverage mixture dispensing system could present the option to set a threshold to the user. The user could then accept the option to put the associated threshold or thresholds in place. The beverage mixture dispensing system could also present an option to implement a specific program with different degrees of tapering (e.g., cold turkey option or gradual weening options).

In specific embodiments of the invention, the ingredient consumption thresholds can be set with respect to specific amounts of time. For example, the thresholds can be set with respect to a period of time such as daily, weekly, monthly, etc. These thresholds could be applied with respect to fixed recurring periods or with respect to a period set by a sliding window (e.g., less than 10 grams from 12:01 am to 12:00 am the next day, or less than 10 grams in any given sliding 24-hour window). These thresholds could also be applied with respect to a fixed or changing period set by the metabolic processing of a specific ingredient by a user (e.g., a period of time equal to the time it takes an average person to bring blood sugar down to a certain level after a given dose of sugar). The metabolic rate could be directly measured (e.g., through a form of biometric testing) or could be derived from an average (e.g., average measurements from a population having similar characteristics to the user). The thresholds can also be set to different amounts depending upon specific times of day, days of the week, etc. (e.g., a lower maximum threshold for alcohol during the week than on the weekend or a lower maximum threshold for caffeine towards the end of the day).

In specific embodiments of the invention, a user can select the period of time to which the thresholds are applied. In embodiments in which the user enters the threshold using a user interface, the period of time could be simultaneously displayed to the user so that they know what amount of time they are setting a threshold for. In specific embodiments of the invention, a user can be given the ability to set both a quantity for the threshold and a period of time for the threshold in order to define an ingredient consumption threshold. This functionality could be provided in the same interface so that a user could quickly specify ingredient consumption levels of different ingredients with respect to different amounts of time, for example, they want to consume less than 500 g of sugar in a week and less than 100 mg of caffeine per day.

The ingredient consumption threshold can be associated with an account. The account can be an account for a user that is tracked locally on the beverage mixture dispensing system or in a server in networked communication with the beverage mixture dispensing system. As the account can be associated with a particular user, the ingredient consumption threshold defined by a user using that account can then be associated with that particular user. The fact that a limit is associated with an account allows the system to track ingredient consumption for a particular user regardless of which device they are using. Accordingly, in specific embodiments of the invention, the account can be accessed from multiple networked beverage mixture dispensing systems (e.g., a device at home, a device in a restaurant, and a device at work) and setting the ingredient consumption threshold on any device on which the user is recognized will update the threshold level associated with the account.

The account could be a user's own account or a subsidiary account such as to provide parental controls for a child's account (e.g., a parent could limit a child's access to alcohol entirely by setting an ingredient maximum threshold to zero and limit access to sugar by setting an ingredient maximum threshold to 50 mg per day) or to provide a dietitian or nutritionists control and monitoring over a patient's ingredient intake. Alternatively, the beverage mixture dispensing system could automatically recognize a user and associate a provisioned threshold with their account or profile.

An ingredient consumption threshold can be associated with an account in various ways. A user could explicitly identify an account to associate a threshold with such as by logging into their account or selecting a profile on a user interface of the system. The user could be recognized in various ways such as based on facial recognition technology, based on the fact that only one user was authorized to use the device (e.g., a beverage mixture dispensing device with only one account or a smartphone owned by a specific user), or based on detecting a drinking vessel that has been assigned to a specific user (e.g., using a radio frequency, visible light, ultraviolet, or infrared encoding, or a weight, visual shape, size, color, texture, pattern, or OCR of written text on or of the vessel). The beverage mixture dispensing system could also be designed to detect the proximity of a user specific device that automatically associates the user of the device with a specific account (e.g., a Bluetooth detection or GPS location of a smartphone, smartwatch, or other wearable of a specific user). Regardless of how the beverage mixture dispensing system determines the identity of a user, once the system has identified a user, a specified ingredient consumption threshold can then be associated with the account and stored in memory.

The ingredients can take on various forms and the thresholds can be defined in various ways based on the form of the ingredients. For example, the ingredients could be any of the concentrated ingredients described in CANAP003 which is incorporated by reference herein in its entirety for all purposes. The ingredients can be solvents or diluents. For example, the ingredients could be solvents such as water. The ingredients could also be classes of individual compounds or components (e.g., artificial sweeteners, sugars, fats, salts etc.). The thresholds could be defined in terms of the mass or volume of pure ingredients (e.g., 50 mg of caffeine or 1 liter of water). Alternatively, the threshold could be defined in terms of the amount of calories they contain (e.g., 50 calories of sugar). Alternatively, the thresholds could be defined in terms of daily values (e.g., 20% of a daily recommended consumption of sugar). The daily allowable values could be stored locally in a beverage dispensing device or be network accessible and could also be associated with a profile of the user (e.g., based on an age or weight of the user). In specific embodiments of the invention, the default thresholds could be 100% of a daily recommended value for a user having the same characteristics as those of the user. Alternatively, the thresholds could be determined using a human body model of absorption of a specific chemical and designed to assure that a level of a given chemical never exceeded a certain level (e.g., do not exceed a BAC of 0.15% or 150 milligrams per deciliter). The human body model could be a physiochemical absorption and transit model comprising pK parameters for a user or class of users. The model could be a 1 or 2 compartment model.

In specific embodiments of the invention, after the ingredient consumption threshold has been set, the beverage mixture dispensing system can be used to mix a beverage using an amount of the ingredient and dispense the beverage for consumption by a user. Accordingly, flow chart 200 includes a step 202 of mixing a beverage using an amount of the ingredient and a step 203 of dispensing the beverage (e.g., into a vessel 220). Sequence of user interface screens 230 and 231 provide an illustration of what could be presented on a user interface of the beverage mixture dispensing system (e.g., display 103) during this process. The mixing of the beverage can include dispensing ingredients from various reservoirs. In the example of the device from FIG. 1A and 1B, the mixing of the beverage could include dispensing ingredients from high volume reservoirs 316, 312, and 315 and concentrated ingredients from the ingredient reservoirs in cartridge 105.

In specific embodiments of the invention, the beverage mixture dispensing device can be configured to automatically mix and dispense the beverage in response to receiving a selection of the beverage from a user. Accordingly, the device will have at its disposal all the information required to determine what amount of any ingredient was added to the beverage. Therefore, at some point after receiving the selection of the beverage, the device can transition to the step of updating an ingredient consumption level for the ingredient. Accordingly, flow chart 200 includes a step 204 of updating an ingredient consumption level for the ingredient by adding the amount to the ingredient consumption level. The ingredient consumption level could be associated with an account (e.g., the specific amount of a specific ingredient dispensed for a given user could be stored as or added to the ingredient consumption level in an entry in a user's account).

The ingredients for which ingredient consumption thresholds are specified and for which consumption is tracked, could be ingredients that are independently dispensed by the device while mixing beverages, ingredients that are jointly dispensed with other ingredients, and/or ingredients that are dispensed from multiple sources on the same device. For example, a user could specify a threshold for sugar, and the device could have a single reservoir of concentrated sucrose solution for sweetening drinks. The amount of the ingredient consumed could then be updated continually based on knowledge of the concentration and the amount of the sucrose solution dispensed from that single reservoir and added to drinks made for a user. The same approach could be taken if the device included a concentrated sucrose solution reservoir and a high-volume diluted sucrose solution reservoir with the usage of either reservoir being used to update a common tally of an amount of sucrose consumed. As another example, a user could specify a threshold for sugar, and the device could have a single reservoir of concentrated strawberry flavoring with sucrose as a component. Again, based on knowledge of the amount of that solution added to drinks for the user, and the concentration of sucrose in that solution, the amount of the ingredient consumed could be updated based thereon. As another example, a user could specify threshold for artificial sweetener, and the device could have multiple reservoirs each containing ingredients with different concentrations of various artificial sweeteners. In this example, based on knowledge of the amount of the various artificial sweeteners in each of those solutions, and knowledge of how much of each of those solutions had been used from those multiple reservoirs, the amount of the ingredient could be updated.

Regardless of how the ingredients are dispensed, in specific embodiments of the invention, the device can be designed to determine, from a recipe of the beverage or from controlling the dispensing of specific ingredients with known characteristics (e.g., concentrations) into the beverage, what amount of each ingredient is mixed in the beverage before it is dispensed. For example, if the device was programmed to dispense citric acid in a 5 mg/L concentrated liquid suspension, and the recipe for a beverage called for 10 ml, the system would know that the amount of the ingredient added was 0.005 mg and would use this amount to update the consumption level for the ingredient. Alternatively, the device could derive the amounts of ingredients for purposes of monitoring ingredient consumption directly from the recipe before the recipe was compiled into dispensing instructions.

The updating of the ingredient consumption level, such as in step 204, can be followed by resetting the consumption level based on the specific ingredient consumption threshold that is being tracked. For example, the ingredient consumption level could be set to zero periodically based on the time period associated with a given ingredient consumption threshold. If the ingredient consumption threshold for a specific ingredient was set on a daily basis, the ingredient consumption level could be returned to zero each night at a given time. The time could be user configurable. Alternatively, in specific embodiments, the time periods are set as sliding windows and the consumption level is reduced by an amount of an ingredient in a specific beverage as soon as the sliding window of time has passed since that specific beverage was consumed (e.g., if a user is tracking consumption using a 24-hour sliding window and it has been just over 24 hours since they consumed a beverage with 10 g of sugar, reduce the consumption level of sugar for that user by 10 g). Alternatively, the ingredient consumption level could otherwise be adjusted downwards based on a sliding window with a duration set by the metabolic rate for a given ingredient in the human body. For example, based on a metabolic model for a specific user, or population of users with similar characteristics, the amount could be reduced if it was determined that a certain amount of the ingredient must have been metabolized by a given time such that an additional dose of the ingredient could be consumed.

The updating of the ingredient consumption level could also be followed by alternative steps for adjusting the level. For example, if feedback was received from a user that a beverage was not actually consumed, any ingredient amount associated with that beverage could be removed from the ingredient consumption level. As another example, if the updating of the ingredient consumption level was conducted upon the ordering of a beverage, but the device included a method for routing the beverage to a waste disposal channel, or otherwise failed to dispense a beverage for consuming, the amount could be removed from the ingredient consumption level. In specific embodiments of the invention, the updating of the ingredient consumption level for the ingredient associated with the account in step 204 is predicated on the dispensing of the beverage in step 203. In such embodiments, if there is an error with mixing or dispensing the beverage, the ingredient consumption level would not need to be corrected based on the fact that the beverage was never actually given to the user. The firmware or hardware of the device could be designed to predicate this updating such as by sending a specialized control signal upon a successful dispense from the firmware of the device to the software to verify that the ingredient consumption level should be updated.

In specific embodiment of the invention, the ingredient consumption level and/or the threshold could be displayed to the user. Accordingly, flow chart 200 includes a step 205 of displaying, on a display, the ingredient consumption level and the ingredient consumption threshold. The two values could be displayed to allow a user to gauge how much of an ingredient they have already consumed against how much they planned to consume. The threshold and the level of consumption can be shown on the display at the same time (for example, the threshold could be illustrated as a gauge and the needle of the gauge could be the level of consumption). However, in alternative embodiments, step 205 could be conducted at different times such that the threshold and levels were displayed at different times (e.g., display the threshold when it is set and display the level consumed after each beverage is ordered). User interface screen 232 provides an illustration of what could be presented on a user interface of the beverage mixture dispensing system (e.g., display 103) during this process. In the illustrated case, the partially filled circle around the profile image in screen 232 indicates a percentage the level of consumption has reached of the threshold.

The information regarding the consumption threshold and consumption level can be displayed at various times. The information could be presented on a display of the device in response to the selection of a beverage icon to display the information, it could be presented to the user in a notification message, or it could be displayed on the display of the device as the beverage is being mixed or after the beverage is dispensed. Displaying the information while the beverage is being mixed and dispensed is beneficial in that the user is presented with useful information instead of simply waiting. The consumption level could also be updated and displayed to the user as part of the selection process of a beverage (i.e., before the beverage was mixed and dispensed) to illustrate to the user how the level of consumption relative to the threshold would be affected if they did proceed to order and consume the beverage.

In addition to displaying the ingredient consumption level and threshold, the values can be stored in a local or network connected database or other structure. The values and all associated information can be used by the system for various purposes such as to modify the recipes of beverages dispensed by the system for particular users in order to keep them within a desired threshold of consumption based on their current level of consumption in terms of numbers of beverages (i.e., slightly decrease the sugar content of each soda consumed by a user that historically consumes 5 sodas per day so that 5 times the sugar content of a single soda made using the modified recipe equals less than the maximum consumption threshold set by that user). Additionally, the data can be made available to other parties such as the main account holder or an account that includes subaccounts for additional users. The data could also be made accessible to other parties such as doctors or nutritionists that are invited to access the information by an account holder. For example, a doctor could securely view, measure, monitor, and even set or modify remotely one or more thresholds for one or more specific ingredients consumed through this system, for a patient under their care who uses the beverage dispensing device, and/or applications and other complimentary associated companion devices. The user information and any associated notifications could be sent to the doctor by email, SMS, instant messaging, or any other format to the doctor's separate devices such as a wearable, smart watch, smartphone, personal computer, or other separate device. Such information could be sent to the doctor without the doctor's proactive action to search for, log in, or lookup this information for their patients.

As specific beverage mixture dispensing systems disclosed herein include a multitude of specific ingredients capable of being used across a wide range of beverages, the ingredient control and monitoring systems disclosed herein can likewise work with multiple ingredients to allow a user to monitor and control how much of each specific ingredient they are consuming. Accordingly, in specific embodiments of the invention, a set of ingredient consumption thresholds associated with an account can be set for a set of ingredients which are then used in comparison with a set of ingredient consumption levels of the set of ingredients associated with the account. For example, a particular user could set a threshold of 50 g for sugar in each day and an additional limit of 100 mg of caffeine per day. The user interface used to specify the separate amounts could be configured to allow a user to select an ingredient from a dropdown menu or an automatically filling search bar and specify individual thresholds for a selected ingredient to achieve this result. The beverage mixture dispensing system could be configured to allow a user to set an ingredient consumption threshold for every different ingredient utilized by the system, or a subset to make the processes of setting limits more acceptable to a user. As such, step 201 can include setting a set of ingredient consumption thresholds, step 204 can include updating a set of ingredient consumption levels for the set of ingredients associated with the account by adding the set of amounts to the set of ingredient consumption levels, and step 205 can include displaying, on a display, the set of ingredient consumption levels and the set of ingredient consumption thresholds. Different settings across multiple ingredients could also be set as pre-set profiles with a user able to set a set of thresholds at the same time by selecting a single profile (e.g., a low acid profile, low sugar profile, low calorie profile, etc.).

Beverage mixture dispensing systems in accordance with this disclosure can assist in controlling ingredient consumption based on the ingredient consumption thresholds in various ways. FIG. 3 includes a logic diagram of various approaches for doing so broken down by a section 301 for approaches used when the system has a minimum consumption threshold and a section 302 for approaches used when the system has a maximum consumption threshold. Certain approaches are used in either situation. Both steps of illustrated approaches can commence with an optional step 303 of receiving an account selection input. This input can be provided explicitly via a user interface (e.g., display 103) or implicitly by determining that a user is currently using the device as explained above with reference to step 201. Step 303 is an optional step because in some cases, such as when the device is only used by one user, there is no need to identify a user to the system in order to track ingredient consumption. Regardless, both sets of approaches also include a step 205 of displaying an ingredient consumption level and an ingredient consumption threshold as described above in FIG. 2. This step is shared by both sections because regardless of whether a user is increasing consumption of an ingredient towards a goal or limiting consumption to keep away from a limit, it is useful to display this information to the user.

In specific embodiments of the invention, the system may recommend beverages to a user in a manner that is likely to increase their consumption of certain ingredients for purposes of assisting users in reaching their desired minimum consumption thresholds. The recommendations could be displayed on a user interface of the device to allow a user to select the recommendation and dispense a recommended beverage. Generally, the system could determine, from an evaluation of the users' consumption history and other characteristics, that they prefer certain beverages to others. These beverages could then be displayed to the user or otherwise provided to the user as options via a user interface. Additionally, in accordance with specific embodiments disclosed herein, an increased consumption of various ingredients is one of the concepts that can be considered in formulating such recommendations. It can be the only concept or it can be considered in combination with other concepts to generate a recommendation. As such, set of approaches 301 includes a step 304 of displaying a recommendation for a beverage that utilizes an ingredient. For example, a user could be provided with beverages by a recommendation system that took not only what they would like to drink, but also what they should drink, into consideration in order to hit their consumption targets. For example, a difference between a consumption level and a minimum consumption threshold could be a feature input to a recommendation engine for recommending beverages on the device. The degree to which the consumption targets were considered in making a recommendation could increase throughout the time period set for reaching those targets. For example, if the targets were set on a daily basis the system could slightly favor beverages with the desired ingredient at the start of the day, but when the day was almost over, the system could be recommending only drinks that used a large amount of those certain ingredients. The step could include displaying the options, or otherwise providing the options, to a user in a manner that allows them to see how much of an impact on their consumption limit the various presented beverages will have.

In specific embodiments of the invention, the system can send notifications to a user to assist them in reaching their desired minimum consumption thresholds. As such, set of approaches 301 include a step 305 of sending a notification to the user. Notifications could also be sent periodically or occasionally to a user to assist them in limiting their consumption below a maximum consumption threshold. The notification could include a presentation of the ingredient consumption level and one or more thresholds being tracked by the system. The notification could also, if pertinent, display the amount of time remaining for the user to meet, or stay under, the threshold. The notification could also indicate an amount of the ingredient in the user's body based on a model of the user's metabolic processes or based on an actual measurement taken of the user's physical condition. Notifications could also be sent to a parent regarding beverage consumption activity of their children, to assist the parent in monitoring, limiting, or managing their children's consumption below a maximum consumption threshold for a specific time period. The notifications could also include the recommendations discussed above with reference to step 304. The notifications could be sent by email, SMS, instant messaging, or any other format to a user's separate devices such as a wearable, smart watch, smartphone, personal computer, or other separate device. The notifications could also be displayed on, or announced from, the device if a user was detected in proximity of the device, or while the user was operating the device.

In specific embodiments of the invention, the system can prevent the dispensing of a beverage that would increase an ingredient consumption level for the ingredient over a maximum ingredient consumption threshold. As such, set of approaches 302 include a step 306 of preventing the dispensing of a beverage. The step can involve removing beverages from a library of beverages that are available for dispensing on the device from being displayed or from being selectable on the device. In specific embodiments, the beverages that are unable to be selected could be hidden entirely as to not entice a user towards their selection. However, in alternative embodiments, the beverages that are unable to be selected could instead be shown as greyed out on a display with text indicating why the beverage was unavailable in order to avoid confusion if a user forgot or was unaware of a specific limit and could not otherwise understand why the selection of beverages had suddenly decreased. In alternative embodiments, the beverage displayed could contain additional information (like a warning message) about the fact that consuming the specific beverage variation as selected would cause the user to exceed their targeted ingredient threshold.

In specific embodiments of the invention, the system can use dynamic variable pricing to encourage (or discourage) a user from dispensing of a beverage that would increase (or decrease) their consumption of a specific ingredient by dynamically changing the pricing paid for beverages that contain the targeted ingredient. Pricing could update via algorithm to dynamically update pricing per beverage to set pricing higher for beverages that contain the targeted ingredient, the closer the user gets to their target threshold to discourage exceeding their target level. Pricing could also update via algorithm to dynamically update pricing per beverage to set pricing lower for beverages that do not contain the targeted ingredient, to encourage users to stay below their target threshold for a specific ingredient.

Figure 3:
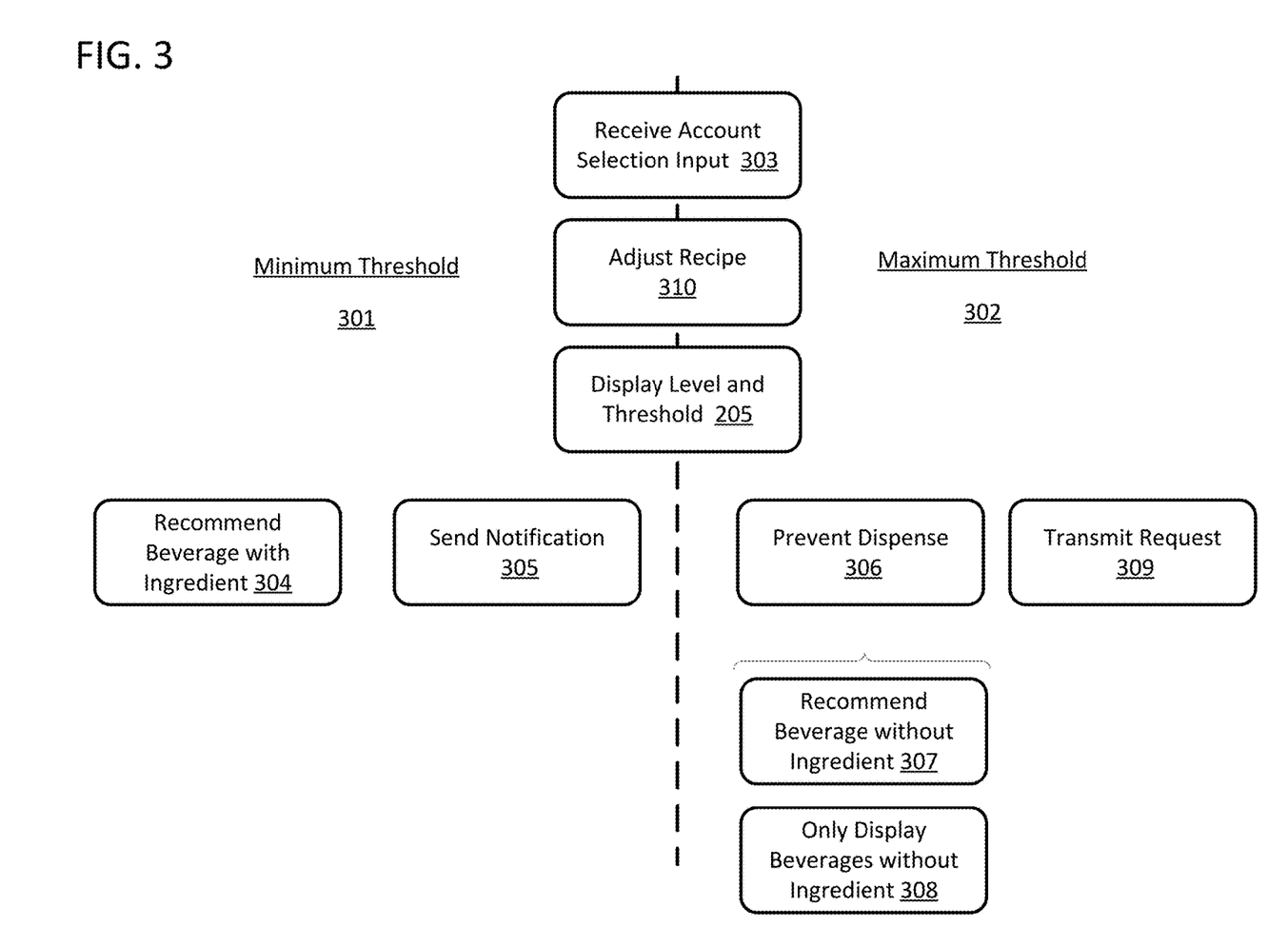
FIG. 3 illustrates a logical diagram for different methods in accordance with specific embodiments of the invention disclosed herein.

FIG. 3 includes a step 307 of recommending beverages without an ingredient. The step can be conducted in a manner similar to step 304 mentioned above but with the alternative objective of decreasing the consumption of one or more ingredients. As such, beverages with certain ingredients would be weighted less favorably even if they would otherwise be recommended for aligning with the user's preferences. The step can include selecting, based on the maximum ingredient consumption threshold and the ingredient consumption level, a set of recommendations for the account; and displaying, on a display, the set of recommendations for the account. The degree by which certain beverages are weighted against being recommended could alter as the threshold was approached with beverages having a given ingredient being less and less likely to be recommended as the threshold was approached. For example, a difference between a maximum consumption threshold and a consumption level could be a feature input to a recommendation engine for recommending beverages on the device with a smaller value for this feature decreasing the likelihood that an associated beverage would be recommended. The ingredient content of the beverage could also be a feature with an increasing value for the beverage decreasing the likelihood that an associated beverage would be recommended.

In specific embodiments of the invention, in which users are charged on a per-drink basis, the beverage mixture dispensing system could adjust a price of certain beverages up or down in order to provide users with an additional motivation to meet their thresholds. For example, if a user set a maximum ingredient consumption threshold for sugar, the price of drinks with sugar could be priced higher as the ingredient consumption level approached that threshold. Beverages with higher sugar content could have their prices increased more than beverages with mild sugar content.

FIG. 3 includes a step 308 of only displaying beverages that will not increase a consumption level over a maximum consumption threshold. This step is shown as an example of step 306 because it is effectively an example of preventing, based on the maximum ingredient consumption threshold and the ingredient consumption level, the display of all beverages, from a set of beverages, that would increase an ingredient consumption level over the maximum ingredient consumption threshold. The set of beverages could be all the beverages that a given beverage dispensing device is capable of dispensing.

FIG. 3 includes a step 309 of transmitting a request. The request could be transmitted when a user attempts to access more of an ingredient than they were allotted via the setting of a threshold. For example, the user could be the holder of a subaccount that is being controlled by a parent, nutritionist, or dietitian. The request could be transmitted to a separate device held by one of those entities and allow them to authorize or deny the dispensing of a beverage that would lead to an ingredient consumption level exceeding a threshold. Such a request might include information about the ingredient levels already consumed during that time period for that user, how much of the ingredient is present in the specific requested beverage, and one or more options to approve or decline the request, which would be sent back to the device and dispensed to the requesting user according to the approval, or not dispensed in the case the request is declined.

FIG. 3 includes a step 310 of adjusting a recipe. The recipe could be adjusted to help a user either meet a minimum threshold or stay under a maximum threshold. The modification of the recipe could be conducted based on a history of usage by the user and adjust the recipe to either increase or decrease an ingredient to assure that the user met their target. For example, an amount of sugar in a recipe could be decreased to allow the user to stay under a threshold for sugar consumption while still having the same number of beverages that they usually have. As another example, a supplement in a recipe could be increased to allow a user to meet a threshold for consumption of the supplement while still having the same number of beverages they usually have. The beverage mixture dispensing systems disclosed herein can be capable of making such modifications automatically without the user being aware of the modification, or of generating such modifications automatically for approval by a user.

In specific embodiments of the invention, the beverage mixture dispensing systems disclosed herein can have access to the information required to execute approaches in accordance with step 310 because they store information either on a single device or in a network accessible database regarding the usage of the beverage mixture dispensing system by a user. For example, the flow chart of FIG. 2 could include storing the thresholds, ingredient consumption levels, changes thereto, and other information associated with the account. The data could be stored along with other metadata like date and time the ingredient was dispensed into a beverage for a given account. In some embodiments, the system may not prevent a user from dispensing a beverage with the ingredient, but instead, provide an informational message or warning to the user that they will, or have exceeded their targeted ingredient threshold. A user could then decide not to proceed with consuming the beverage. However, in these embodiments, the user could explicitly be given the option to execute step 310 by either manually adjusting the recipe or selecting an automatic modification such that the recipe was changed such that it would not increase a consumption level over a threshold.

Figure 4:
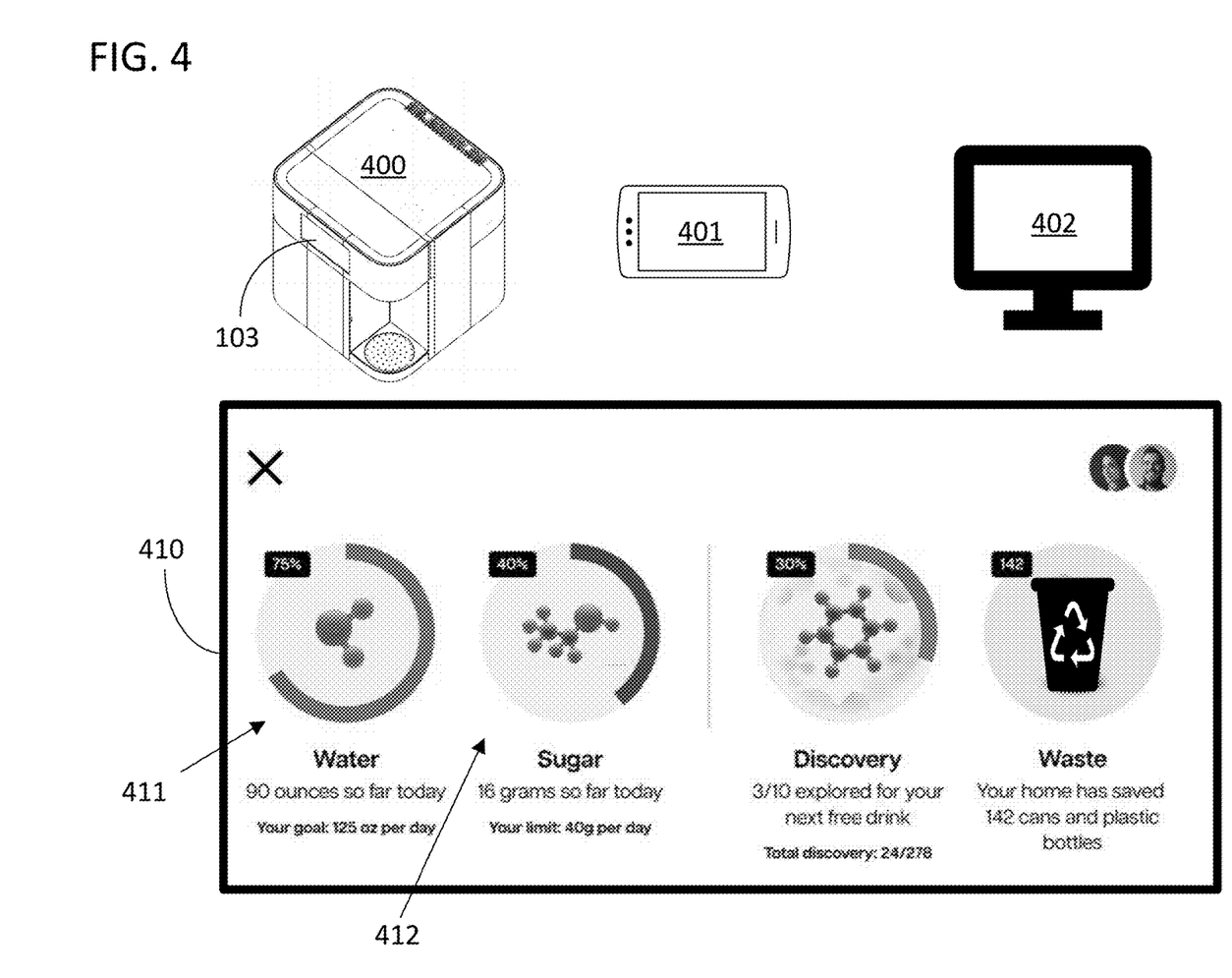
FIG. 4 illustrates an example user interface screen in accordance with specific embodiments of the invention disclosed herein.

FIG. 4 illustrates an exemplary user interface screen 410 that can be displayed by a beverage mixture dispensing system. For example, the user interface screen 410 could be displayed on a display 103 of a beverage mixture dispensing device 400, a display of a smartphone 401, or a display of a personal computer 402. As shown, the user interface screen 410 includes a representation 411 of a minimum ingredient consumption threshold and associated consumption level. In this case, the display includes both a graphical and textual representation of both values which are provided to assist a user with increasing their water intake. Also as shown, the user interface screen 410 includes a representation 412 of a maximum ingredient consumption threshold and associated consumption level. In this case, the display includes both a graphical and textual representation of both values provided in order to assist a user with minimizing their sugar intake.

A controller, as used in this disclosure, can include one or more processors that can be distributed locally within a device or remotely across a system with servers and/or separate devices. For example, one or more components of the system, such as valves, pumps, and sensors can be associated to individual microcontrollers that can control their operations and interaction with other components of the system. In specific embodiments of the invention, the controller can be a control system for the overall device even if the various control elements are separately programmed and are not part of a common control hierarchy. The controller can have access to one or more memories that store the instructions for the controllers to execute any of the methods disclosed herein. The memories can also store information for the system, such as a library of recipes, reference values such as the identity, concentration, and other characteristics of the ingredients stored in the ingredient reservoirs of the device.

While the specification has been described in detail with respect to specific embodiments of the invention, it will be appreciated that those skilled in the art, upon attaining an understanding of the foregoing, may readily conceive of alterations to, variations of, and equivalents to these embodiments. For example, while the disclosure was mainly directed to systems for dispensing beverages, devices that are designed to formulate solid foods can also benefit from the ingredient monitoring and control systems disclosed herein. As another example, many examples in this disclosure were provided of ingredients having a maximum consumption threshold or a minimum consumption threshold. However, some ingredients may have both minimum and maximum consumption thresholds and combinations of the approaches described above can be used for these ingredients (e.g., a given salt may have a minimum consumption threshold and a maximum consumption threshold and the consumption level could be displayed with reference to both thresholds). Any of the method disclosed herein can be executed by a processor in combination with a computer readable media storing instructions for the methods in combination with the other hardware elements described above. These and other modifications and variations to the present invention may be practiced by those skilled in the art, without departing from the scope of the present invention, which is more particularly set forth in the appended claims.

What is claimed is:

1. A method, for operating a beverage mixture dispensing system, comprising:
setting an ingredient consumption threshold for an ingredient, wherein the ingredient consumption threshold is associated with an account;
mixing a beverage using an amount of the ingredient;
dispensing the beverage;
updating an ingredient consumption level associated with the account, by adding the amount to the ingredient consumption level; and
displaying, on a display, the ingredient consumption level and the ingredient consumption threshold.

2. The method of claim 1, further comprising:
setting a set of ingredient consumption thresholds for a set of ingredients, wherein the set of ingredient consumption thresholds is associated with the account, and wherein mixing the beverage uses a set of amounts of the set of ingredients;
updating a set of ingredient consumption levels for the set of ingredients associated with the account by adding the set of amounts to the set of ingredient consumption levels; and
displaying, on a display, the set of ingredient consumption levels and the set of ingredient consumption thresholds.

3. The method of claim 1, wherein:
the ingredient consumption threshold is a maximum ingredient consumption threshold; and
the method further comprises preventing the dispensing of a second beverage that would increase the ingredient consumption level for the ingredient over the maximum ingredient consumption threshold.

4. The method of claim 1, wherein:
the ingredient consumption threshold is a minimum ingredient consumption threshold;
the method further comprises displaying, on the display, a recommendation for the account; and
the recommendation utilizes the ingredient.

5. The method of claim 1, wherein:
the updating of the ingredient consumption level for the ingredient associated with the account by adding the amount to the ingredient consumption level is predicated on the dispensing of the beverage.

6. The method of claim 1, further comprising:
receiving an account selection input, via the display of the beverage mixture dispensing system, wherein the account selection input selects the account;
displaying, on the display, a set of recommendations for the account; and
wherein the ingredient consumption threshold is associated with the account due to the account selection input.

7. The method of claim 1, further comprising:
receiving an account selection input, via a radio frequency reader of the beverage mixture dispensing system, wherein the account selection input selects the account; and wherein the radio frequency reader receives the account selection input from a beverage container associated with the account.

8. The method of claim 1, wherein:
the displaying of the ingredient consumption level and the displaying of the ingredient consumption threshold are conducted simultaneously; and
the ingredient consumption level is displayed as a percentage of the ingredient consumption threshold.

9. The method of claim 1, wherein:
the ingredient consumption threshold is a maximum ingredient consumption threshold;
the method further comprises: selecting, based on the maximum ingredient consumption threshold and the ingredient consumption level, a set of recommendations for the account;
the method further comprises: displaying, on the display, the set of recommendations for the account; and
the set of recommendations are for beverages that would not increase the ingredient consumption level over the maximum ingredient consumption threshold.

10. The method of claim 1, wherein:
the ingredient consumption threshold is a maximum ingredient consumption threshold;
the beverage mixture dispensing system has access to a set of beverages; and
the method further comprises preventing, based on the maximum ingredient consumption threshold and the ingredient consumption level, the display of all beverages from the set of beverages that would increase the ingredient consumption level over the maximum ingredient consumption threshold.

11. A beverage mixture dispensing system comprising:
a dispenser;
a display;
a set of ingredient reservoirs storing a respective set of ingredients; and
one or more computer readable media storing instructions which, when executed by one or more processors, cause the beverage mixture dispensing system to:
set an ingredient consumption threshold for an ingredient, wherein the ingredient consumption threshold is associated with an account, and wherein the ingredient is in the respective set of ingredients;
mix a beverage using an amount of the ingredient from the set of ingredient reservoirs;
dispense the beverage using the dispenser;
update an ingredient consumption level associated with the account by adding the amount to the ingredient consumption level; and
display, on the display, the ingredient consumption level and the ingredient consumption threshold.

12. The beverage mixture dispensing system of claim 11, wherein:
the set of ingredient reservoirs is a set of at least 20 ingredient reservoirs; and
the set of respective ingredients is a set of at least at least 20 molecular entities independently suspended in liquid water in at least 20 ingredient reservoirs.

13. The beverage mixture dispensing system of claim 11, wherein the one or more computer readable media further store instructions which, when executed by the one or more processors, cause the beverage mixture dispensing system to:
set a set of ingredient consumption thresholds for a set of ingredients, wherein the set of ingredient consumption thresholds is associated with the account, and wherein mixing the beverage uses a set of amounts of the set of ingredients;
update a set of ingredient consumption levels for the set of ingredients associated with the account by adding the set of amounts to the set of ingredient consumption levels; and
display, on a display, the set of ingredient consumption levels and the set of ingredient consumption thresholds.

14. The beverage mixture dispensing system of claim 11, wherein:
the ingredient consumption threshold is a maximum ingredient consumption threshold; and
the one or more computer readable media further store instructions which, when executed by the one or more processors, cause the beverage mixture dispensing system to prevent the dispensing of a second beverage that would increase the ingredient consumption level for the ingredient over the maximum ingredient consumption threshold.

15. The beverage mixture dispensing system of claim 11, wherein:
the ingredient consumption threshold is a minimum ingredient consumption threshold;
the one or more computer readable media further store instructions which, when executed by the one or more processors, cause the beverage mixture dispensing system to display, on the display, a recommendation for the account; and
the recommendation utilizes the ingredient.

16. The beverage mixture dispensing system of claim 11, wherein:
the updating of the ingredient consumption level for the ingredient associated with the account by adding the amount to the ingredient consumption level is predicated on the dispensing of the beverage.

17. The beverage mixture dispensing system of claim 11, wherein:
the one or more computer readable media further store instructions which, when executed by the one or more processors, cause the beverage mixture dispensing system to: receive an account selection input, via the display of the beverage mixture dispensing system, wherein the account selection input selects the account; and display, on the display, a set of recommendations for the account; and
the ingredient consumption threshold is associated with the account due to the account selection input.

18. The beverage mixture dispensing system of claim 11, further comprising:
a radio frequency reader;
wherein the one or more computer readable media further store instructions which, when executed by the one or more processors, cause the beverage mixture dispensing system to receive an account selection input, via the radio frequency reader of the beverage mixture dispensing system, wherein the account selection input selects the account; and
wherein the radio frequency reader receives the account selection input from a beverage container associated with the account.

19. The beverage mixture dispensing system of claim 11, wherein:
the displaying of the ingredient consumption level and the displaying of the ingredient consumption threshold are conducted simultaneously; and the ingredient consumption level is displayed as a percentage of the ingredient consumption threshold.

20. The beverage mixture dispensing system of claim 11, wherein:
the ingredient consumption threshold is a maximum ingredient consumption threshold;
the one or more computer readable media further store instructions which, when executed by the one or more processors, cause the beverage mixture dispensing system to select, based on the maximum ingredient consumption threshold and the ingredient consumption level, a set of recommendations for the account;
the one or more computer readable media further store instructions which, when executed by the one or more processors, cause the beverage mixture dispensing system to:
display, on the display, the set of recommendations for the account; and
the set of recommendations are for beverages that would not increase the ingredient consumption level over the maximum ingredient consumption threshold.

21. The beverage mixture dispensing system of claim 11, wherein:
the ingredient consumption threshold is a maximum ingredient consumption threshold;
the beverage mixture dispensing system has access to a set of beverages; and
the one or more computer readable media further store instructions which, when executed by the one or more processors, cause the beverage mixture dispensing system to prevent, based on the maximum ingredient consumption threshold and the ingredient consumption level, the display of all beverages from the set of beverages that would increase the ingredient consumption level over the maximum ingredient consumption threshold.

22. One or more computer-readable media storing instructions which, when executed by one or more processors in a beverage mixture dispensing system, cause the beverage mixture dispensing system to execute a method comprising:
setting an ingredient consumption threshold for an ingredient, wherein the ingredient consumption threshold is associated with an account;
mixing a beverage using an amount of the ingredient;
dispensing the beverage;
updating an ingredient consumption level associated with the account, by adding the amount to the ingredient consumption level; and
displaying, on a display, the ingredient consumption level and the ingredient consumption threshold.

23. The one or more computer-readable media of claim 22, wherein the method further comprises:
setting a set of ingredient consumption thresholds for a set of ingredients, wherein the set of ingredient consumption thresholds is associated with the account, and wherein mixing the beverage uses a set of amounts of the set of ingredients;
updating a set of ingredient consumption levels for the set of ingredients associated with the account by adding the set of amounts to the set of ingredient consumption levels; and
displaying, on a display, the set of ingredient consumption levels and the set of ingredient consumption thresholds.

24. The one or more computer-readable media of claim 22, wherein:
the ingredient consumption threshold is a maximum ingredient consumption threshold; and
the method further comprises preventing the dispensing of a second beverage that would increase the ingredient consumption level for the ingredient over the maximum ingredient consumption threshold.

25. The one or more computer-readable media of claim 22, wherein:
the ingredient consumption threshold is a minimum ingredient consumption threshold;
the method further comprises displaying, on the display, a recommendation for the account; and
the recommendation utilizes the ingredient.

26. The one or more computer-readable media of claim 22, wherein:
the updating of the ingredient consumption level for the ingredient associated with the account by adding the amount to the ingredient consumption level is predicated on the dispensing of the beverage.

27. The one or more computer-readable media of claim 22, wherein the method further comprises:
receiving an account selection input, via a radio frequency reader of the beverage mixture dispensing system, wherein the account selection input selects the account; and
wherein the radio frequency reader receives the account selection input from a beverage container associated with the account.

28. The one or more computer-readable media of claim 22, wherein:
the displaying of the ingredient consumption level and the displaying of the ingredient consumption threshold are conducted simultaneously; and
the ingredient consumption level is displayed as a percentage of the ingredient consumption threshold.

29. The one or more computer-readable media of claim 22, wherein:
the ingredient consumption threshold is a maximum ingredient consumption threshold;
the method further comprises selecting, based on the maximum ingredient consumption threshold and the ingredient consumption level, a set of recommendations for the account;
the method further comprises displaying, on the display, the set of recommendations for the account; and
the set of recommendations are for beverages that would not increase the ingredient consumption level over the maximum ingredient consumption threshold.

30. The one or more computer-readable media of claim 22, wherein:
the ingredient consumption threshold is a maximum ingredient consumption threshold;
the beverage mixture dispensing system has access to a set of beverages; and
the method further comprises preventing, based on the maximum ingredient consumption threshold and the ingredient consumption level, the display of all beverages from the set of beverages that would increase the ingredient consumption level over the maximum ingredient consumption threshold.

* * * * *